United States Patent
Castanedo et al.

(12) 
(10) Patent No.: US 6,341,726 B1
(45) Date of Patent: Jan. 29, 2002

(54) APPARATUS FOR INSPECTING ELEMENTS ON TRANSPORT DEVICE

(75) Inventors: Agustin Del Rio Castanedo; Omar Benjamin Garcia Puga; Marco Antonio Martinez Cardenas, all of Jalisco (MX)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/338,845

(22) Filed: Jun. 23, 1999

(51) Int. Cl.[7] .................................................. G06K 7/10
(52) U.S. Cl. ...................... 235/462.13; 235/376; 29/593
(58) Field of Search ........................ 235/462.13, 462.14, 235/375, 376, 462.08, 462.09; 29/740, 739, 720, 832, 701, 709, 593; 700/213, 214, 215, 218; 422/63, 65, 67; 271/298

(56) References Cited

U.S. PATENT DOCUMENTS

| | | | |
|---|---|---|---|
| 5,357,095 A | * 10/1994 | Weyrauch et al. | ........... 235/494 |
| 5,424,030 A | * 6/1995 | Ushikubo | ..................... 422/64 |
| 5,455,870 A | 10/1995 | Sepai et al. | |
| 5,463,227 A | 10/1995 | Stern et al. | |
| 5,600,150 A | 2/1997 | Stern et al. | |
| 5,646,389 A | 7/1997 | Bravman et al. | |
| 5,663,545 A | * 9/1997 | Marquiss | ..................... 235/375 |
| 5,691,544 A | 11/1997 | Stern et al. | |
| 5,749,205 A | * 5/1998 | Edwards et al. | .............. 53/542 |
| 5,793,051 A | 8/1998 | Stern et al. | |
| 5,818,061 A | 10/1998 | Stern et al. | |
| 5,985,215 A | * 11/1999 | Sakazume et al. | ............. 422/67 |
| 6,005,482 A | * 12/1999 | Maoran et al. | .......... 340/568.8 |

FOREIGN PATENT DOCUMENTS

| | | | |
|---|---|---|---|
| JP | 59-226865 A | * | 12/1984 |
| JP | 6111086 A | | 4/1994 |
| JP | 8287213 A | | 1/1996 |
| JP | 8194802 A | | 7/1996 |
| JP | 09-205291 | * | 8/1997 |
| JP | 2000-171471 | * | 6/2000 |

OTHER PUBLICATIONS

Western Electric, "Apparatus for Counting Chips in Compliant Tape", Techanical Digest No. 38, Apr. 1975.
IBM Technical Disclosure Bulletin, "Automatic Green Sheet Counter", vol. 28, No. 11, Apr. 1986.

* cited by examiner

*Primary Examiner*—Michael G. Lee
*Assistant Examiner*—Diane S. Lee
(74) *Attorney, Agent, or Firm*—Douglas R. Millett; Bracewell & Patterson, L.L.P.

(57) ABSTRACT

A tray mapper uses an optical sensing array to detect if a head gimbal assembly suspension is located in each of the available positions in a shipping tray. Each tray to be inspected is placed on the mapper and located in a scanning position. A pair of electro-mechanical switches send a signal to a microprocessor indicating that the next tray is ready to be processed. A bar code reader mounted on the mapper reads a label on the tray to access information regarding the tray and its contents from a central database. After the tray label is read, an optical sensor located beneath each position on the tray detects the presence or absence of a part. The microprocessor reads the status of each of the sensors against the values associated with the tray label. This information is used by the operator's data terminal software to decide if the tray should be accepted or rejected. The operator is informed of the proper action via a text message on his terminal. The operator then handles the tray accordingly.

21 Claims, 3 Drawing Sheets

APPARATUS FOR INSPECTING ELEMENTS ON TRANSPORT DEVICE

BACKGROUND OF THE INVENTION

1. Technical Field

This invention relates in general to inspecting electrical components during manufacturing and in particular to the final inspection of shipping trays of head gimbal assemblies after they are manufactured.

2. Background Art

In manufacturing, it is not uncommon for quantities of subassemblies or other elements to be moved from one processing station to the next on a transport device. When the elements leave the sending station, they typically have been counted or somehow configured and are expected to arrive at the receiving station in the identical condition. When there is a discrepancy in an arriving shipment, the manufacturing sequence is usually interrupted and may be shut down.

For example, in the final inspection area of a head gimbal assembly manufacturing operation, an operator visually inspects the number of suspensions in each shipping tray before it passes to the packing station. The purpose of this visual inspection is to ensure that the information on the data collection or tracking system is accurate.

The inspector takes a tray from a stack and, using a hand held scanner, scans the bar code label that identifies the tray. After waiting for the tray mapping information to appear on the screen of his nearby data terminal, the inspector visually compares what the system says should be on the tray, against what is actually on the tray. This procedure is then repeated for each tray in the stack. If no inconsistencies are found between the system information and the actual, physical inspection, the complete stack is sent to the packing station. Although this manual procedure is workable, a faster and more accurate system is desirable.

Therefore, it is a feature of the present invention to provide an automated system for inspecting trays of head gimbal assemblies to verify assembly-generated values.

It is another feature of the present invention to provide this inspection at higher speeds that manual inspections while reducing inspection errors.

SUMMARY OF THE INVENTION

A tray mapper uses an optical sensing array to detect if a head gimbal assembly suspension is located in each of the available positions in a shipping tray. Each tray to be inspected is placed on the mapper and located in a scanning position. A pair of electromechanical switches send a signal to a microprocessor indicating that the next tray is ready to be processed.

A bar code reader mounted on the mapper reads a label on the tray to access information regarding the tray and its contents from a central database. After the tray label is read, an optical sensor located beneath each position on the tray detects the presence or absence of a part. The microprocessor reads the status of each of the sensors against the values associated with the tray label. This information is used by the operator's data terminal software to decide if the tray should be accepted or rejected. The operator is informed of the proper action via a text message on his terminal. The operator then handles the tray accordingly.

BRIEF DESCRIPTION OF THE DRAWINGS

So that the manner in which the features, advantages and objects of the invention, as well as others which will become apparent, are attained and can be understood in more detail, more particular description of the invention briefly summarized above may be had by reference to the embodiment thereof which is illustrated in the appended drawings, which drawings form a part of this specification. It is to be noted, however, that the drawings illustrate only a preferred embodiment of the invention and is therefore not to be considered limiting of its scope as the invention may admit to other equally effective embodiments.

BEST MODE FOR CARRYING OUT THE INVENTION

Figure 1:
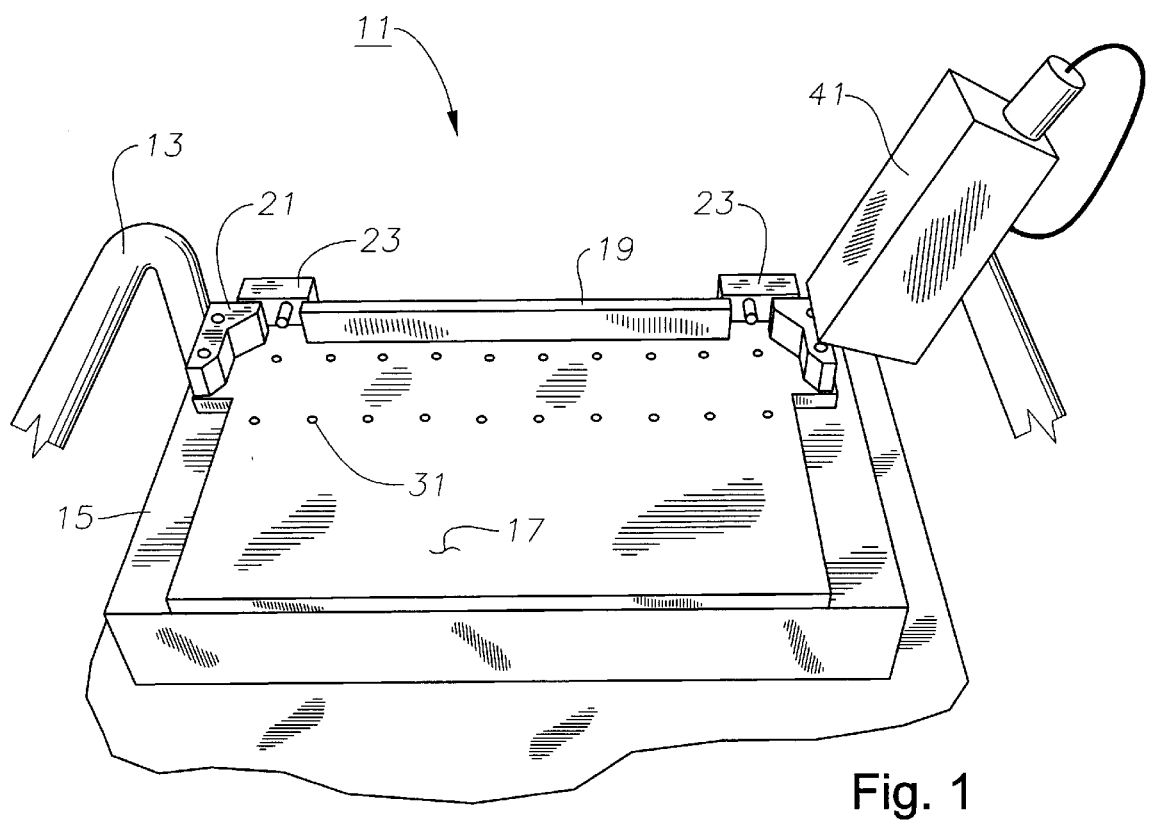
FIG. 1 is a front isometric view of a tray mapper constructed in accordance with the invention.
Figure 2:
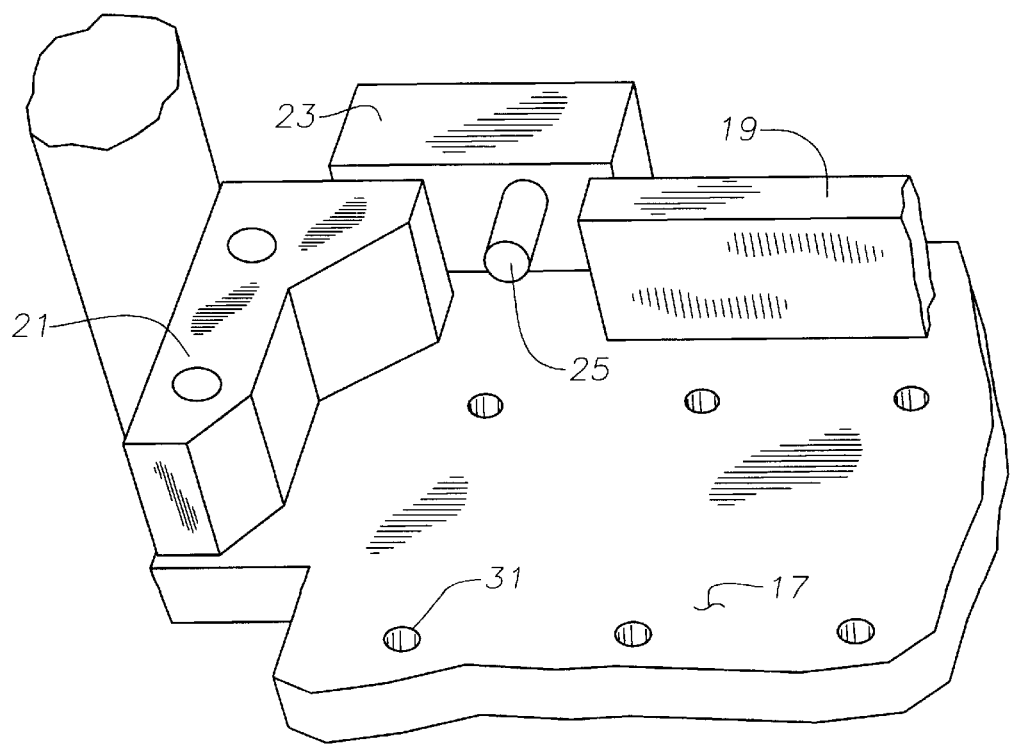
FIG. 2 is an enlarged isometric view of a switch on the tray mapper of FIG. 1.

Referring to FIGS. 1 and 2, a t ray mapper 11 is mounted to a support rack 13 as shown. Mapper 11 has a generally rectangular body 15 with a smooth, flat upper surface 17. An elongated backstop 19 is mount ed to the rearward end of surface 17 along the back edge of body 15. A side wall 21 is mounted to body 15 on each lateral side edge of backstop 19 and surface 17. Side walls 21 extend forward a slight distance from the rearward end of surface 17 and are spaced apart from one another by a precise distance. An electromechanical switch 23 is located at each of the two interfaces between backstop 19 and the side walls 21. Each switch 23 has a short, movable actuator 25 that protrudes forward over surface 17. Switches 23 are electrically connected to a microprocessor 27 (FIG. 5) located within body 15.

Figure 5:
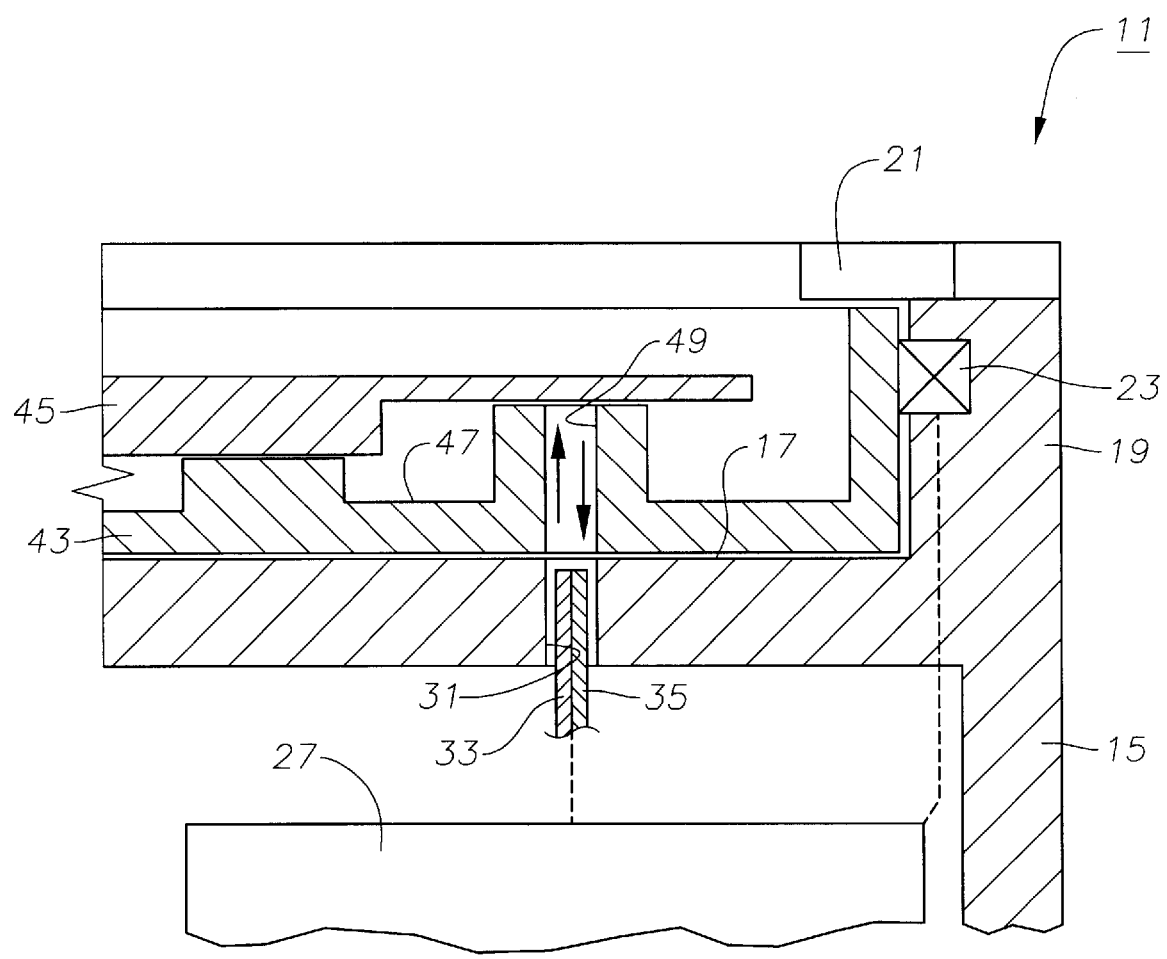
FIG. 5 is a sectional side view of the tray mapper, shipping tray and a suspension of FIG. 4 taken along the line 5—5 of FIG. 4.

Surface 17 of mapper 11 has a plurality of holes 31 that are symmetrically spaced apart from one another. In the embodiment shown, there are twenty holes 31 in surface 17. As shown in FIG. 5, each hole 31 contains a duplex optic fiber 33 which emits visible light. Each optic fiber 33 also contains a photocell light detector 35 for detecting the reflected light of optic fiber 33 and emitting a return signal to microprocessor 27 in response thereto. Tray mapper 11 also comprises a conventional laser bar code reader 41 (FIG. 1) which is mounted on one of the sides of body 15. Reader 41 is operable in response to a trigger signal from microprocessor 27.

Figure 3:
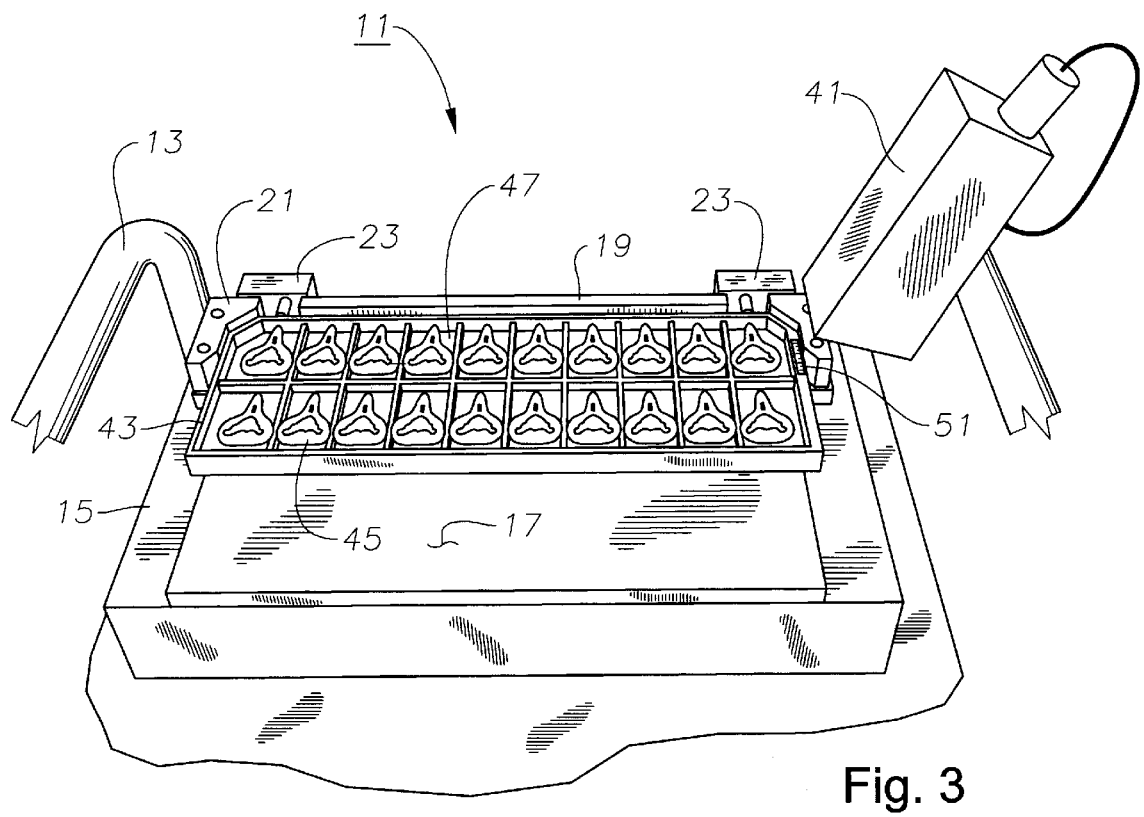
FIG. 3 is a front isometric view of a suspension shipping tray mounted in the tray mapper of FIG. 1.
Figure 4:
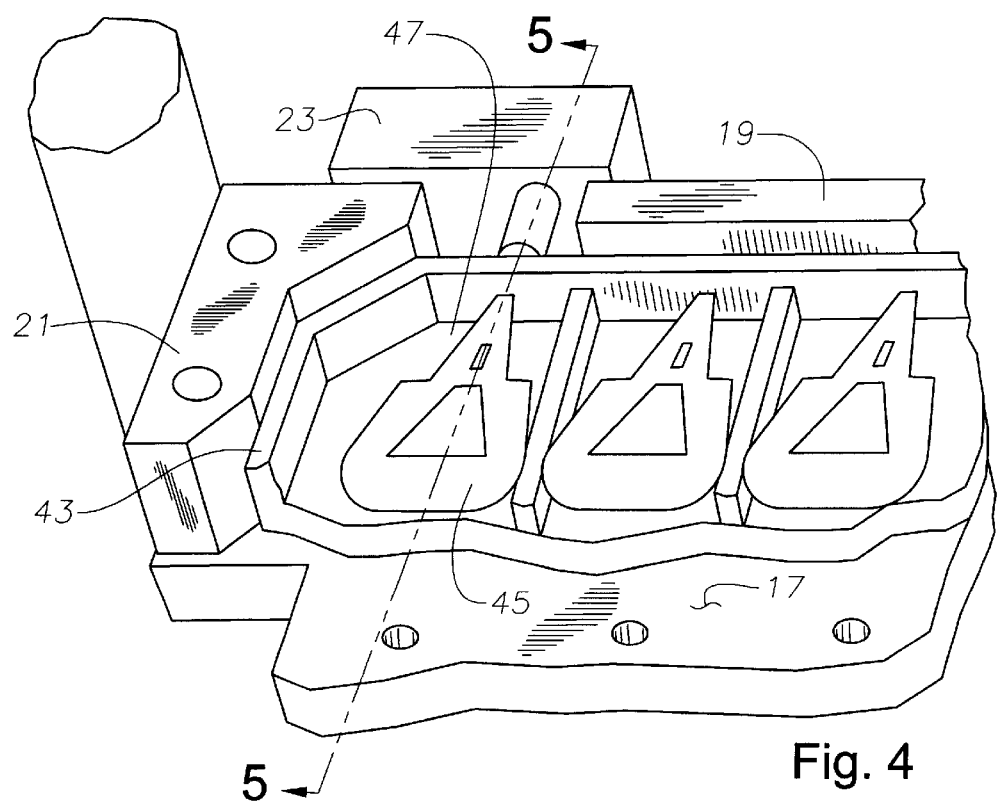
FIG. 4 is an enlarged isometric view of the shipping tray and tray mapper of FIG. 3 showing the switch of FIG. 2.

In operation (FIGS. 3–5), an operator places a shipping tray 43 for head gimbal assembly suspensions 45 on surface 17 of tray mapper 11 for inspection. In the embodiment shown, tray 43 is an elongated rectangular member with twenty positions 47 for supporting suspensions 45 and limiting them from excessive movement. Each position 47 contains a vertical through hole 49 (FIG. 5). The operator slides tray 43 toward backstop 19 and between side walls 21. Side walls 21 are precisely spaced apart to closely receive the lateral side edges of tray 43. When the rear edge of tray 43 abuts backstop 19, actuators 25 will be triggered to notify microprocessor 27 that tray 43 is in properly located in a scanning position for inspection. Microprocessor 27 continuously validates the signals to avoid system malfunctions. At this stage, each hole 49 coaxially aligns with one hole 31 in surface 17 (FIG. 5).

With tray 43 in the scanning position, microprocessor 27 actuates bar code reader 41 to scan and read a bar code label 51 which is precisely located along the side edge of tray 43. Label 51 identifies tray 43 and, thus, the number of suspensions 45 and each of their positions based upon prior information supplied during manufacturing and assembly. The information associated with label 51 is sent to a PC host data terminal through serial port (not shown).

Once label 51 has been read, each part or suspension 45 must be physically detected in order to verify the accuracy of the label information. Microprocessor 27 signals each optic fiber 33 to emit a visible light which is reflected back by the metal surface of the associated suspension 45. The reflected light is collected by photocell light detector 35 through the same optic fiber 33 and an electrical signal is generated in accordance with the presence or absence of the part. Microprocessor 27 reads the status of each one of the sensors in the array, translates this information into a readable text message for the operator to observe, and sends it to the PC host through the serial port. The PC host uses the information provided by tray mapper 11 to verify that the previous information provided through label 51 is accurate. If the information is consistent, tray 43 is accepted. If the information is inconsistent, tray 43 is rejected. Tray 43 is then removed from mapper 11 and processed accordingly, and the procedure is repeated for other trays 43.

The invention has several advantages. The tray mapper provides a fast, efficient and accurate means for inspecting trays of head gimbal assembly suspensions. The elements of the mapper are precisely toleranced to yield improved performance over the prior art manual inspection method.

While the invention has been shown or described in only some of its forms, it should be apparent to those skilled in the art that it is not so limited, but is susceptible to various changes without departing from the scope of the invention.

We claim:

1. An apparatus, comprising:
   a tray having a plurality of positions configured in a two-dimensional array, each of the positions being capable of supporting an element, and wherein at least one of the positions is adapted to support an element;
   a label affixed to the tray;
   a base having a receptacle for closely receiving the tray;
   a reader fixedly mounted with respect to the base for scanning the label on the tray;
   a plurality of sensors in a two-dimensional array mounted to the base adjacent to the receptacle, each of sensors being precisely located to align in at least two dimensions with one of the positions on the tray when the tray is in the receptacle, and each of the sensors being adapted to detect the presence or absence of an element in each of the positions; and
   a microprocessor connectable to the reader and the sensors for processing information associated with the label regarding the elements and the information collected by the sensors and generating a response thereto.

2. The apparatus of claim 1 wherein each of the sensors comprises a single optic fiber with a photocell light detector for sending and receiving an optical signal from a single location.

3. The apparatus of claim 2 wherein the optic fibers utilize visible light.

4. The apparatus of claim 1 wherein the receptacle comprises a planar upper surface on the base with a back wall and a pair of side walls.

5. The apparatus of claim 1 wherein the reader comprises a bar code reader and the label comprises bar coded information.

6. The apparatus of claim 1 wherein each of the sensors is mounted in a hole in the receptacle.

7. The apparatus of claim 1, further comprising an electromechanical switch fixedly mounted with respect to the receptacle for detecting when the tray is in the receptacle.

8. The apparatus of claim 7, wherein the microprocessor signals the reader to read the label in response to actuation of the switch.

9. The apparatus of claim 1 wherein the response generated by the microprocessor is processed to accept the tray when the information associated with the label matches the information collected by the sensors, and wherein the response generated by the microprocessor is processed to reject the tray when the information associated with the label is inconsistent with the information collected by the sensors.

10. A method for inspecting a transport device, comprising:
   (a) providing a base with a receptacle and a plurality of sensors fixedly mounted with respect to the receptacle in a two-dimensional array, a microprocessor, and a transport device with a label and a plurality of positions wherein a plurality of the positions each contain an element to form a two-dimensional array of elements;
   (b) placing the transport device in the receptacle such that each of the positions on the transport device aligns with one of the sensors in two-dimensional alignment;
   (c) reading the label on the transport device;
   (d) detecting the presence or absence of an element with the sensors in each of the positions on the transport device; and then
   (e) processing information associated with the label regarding the elements and the information collected by the sensors and generating a response thereto.

11. The method of claim 10 wherein step (d) comprises emitting visible light with each of the sensors and detecting any reflection thereof off of the elements from a single location.

12. The method of claim 10 wherein step (c) comprises scanning a bar code on the label with a bar code reader.

13. The method of claim 10 wherein step (e) comprises processing the response to accept or reject the transport device.

14. The method of claim 10 wherein step (b) further comprises detecting the presence of the transport device.

15. The method of claim 14 wherein step (b) occurs before step (c), and step (c) occurs before step (d).

16. An inspection system for determining the presence of all intended elements for being transported as a unit, comprising:
   a tray having a plurality of element positions for receiving intended elements to form a two-dimensional array of the intended elements, and a bar coded label for identifying information about whether each element position includes an intended element;
   a base having a receptacle for the tray;
   a bar code reader for scanning the label and developing a signal consistent with the label;
   sensors mounted in the base adjacent to the receptacle in a two-dimensional array, there being a respective sensor correspondingly aligned with each element position on the tray, each sensor adapted to emit a signal in response to the presence or absence of an element in respective element positions while the intended elements are arrayed in two dimensions; and
   a microprocessor connected to the sensors and to the reader for processing the reader signal and the information regarding actual element presence determined by the sensor signals and generating a response thereto, and wherein said response is adapted to be processed and displayed by computer means.

17. The inspection system of claim 16 wherein each of the sensors comprises a single optic fiber with a visible light photocell detector for sending and receiving an optical signal from a single location.

18. The inspection system of claim 16 wherein the receptacle comprises a planar upper surface on the base with alignment features along its side and rear edges.

19. The inspection system of claim 16 wherein the receptacle has a plurality of holes and one of the sensors is mounted in each of the holes.

20. The inspection system of claim 16, further comprising an electro-mechanical switch fixedly mounted with respect to the receptacle for detecting when the tray is in the receptacle.

21. The inspection system of claim 20, wherein the microprocessor signals the reader to read the label in response to actuation of the switch.

* * * * *